United States Patent [19]

Kojima

[11] 4,109,644

[45] Aug. 29, 1978

[54] MINIATURE IMPLANTABLE ULTRASONIC ECHOSONOMETER

[75] Inventor: Gilbert K. Kojima, Mountain View, Calif.

[73] Assignee: The United States of America as represented by the United States National Aeronautics and Space Administration, Washington, D.C.

[21] Appl. No.: 758,721

[22] Filed: Jan. 12, 1977

[51] Int. Cl.$^2$ ............................................. A61B 10/00
[52] U.S. Cl. ................................ 128/2 V; 128/2.05 Z; 128/2.1 A
[58] Field of Search .................. 128/2 P, 2 V, 2.05 Z, 128/2.05 E, 2.1 A

[56] References Cited

U.S. PATENT DOCUMENTS

| | | | |
|---|---|---|---|
| 3,662,758 | 5/1972 | Glover | 128/2.1 A X |
| 3,757,770 | 9/1973 | Brayshaw et al. | 128/2.1 A X |
| 3,763,463 | 10/1973 | Muir | 128/2 V X |
| 3,827,115 | 8/1974 | Bom | 128/2 V X |
| 3,853,117 | 12/1974 | Murr | 128/2 V |
| 3,872,858 | 3/1975 | Hudson et al. | 128/2 V |

OTHER PUBLICATIONS

Lee, R. D. et al., "Miniature Implantable Sonomicrometer System," Journal of Applied Physiology V. 28 #1, Jan. 1970 pp. 110–112.
"Animal Monitoring" – Medical Electronics 12/66 p. 4.
Frescura, B. L. et al., "Micropower Integrated Circuits for Implantable Bi-directional Blood Flowmeter," IEEE Jrnl. of Sol. St Ckts., vol. SC-11 #6 pp. 817–825, 12/76.
Kadefors, R. "Controlled External Powering of Miniature Chronically Implanted Biotelementry Devices," IEEE Biomed Engr. Trans. V. BME-23, #23/76 pp. 124–129.
Eversden, I. D., "Detecting Intra-Cranial Pressure Waves with Ultrasound," Ultrasonics Dig. of 3rd Intnl. Conf. on Med. Physics Göteborg, Sweden 1972.
Rader, R. et al., "An Implantable Blood Pressure and Flow Transmitter," IEEE Biomed Engr. Trans., vol. BME-20, #1, Jan. 1973.

Primary Examiner—Robert W. Michell
Assistant Examiner—Francis J. Jaworski
Attorney, Agent, or Firm—Darrell G. Brekke; John R. Manning; Armand McMillan

[57] ABSTRACT

A miniature echosonometer adapted for implantation in the interior of an animal for imaging the internal structure of an organ, tissue or vessel. The echosonometer includes a receiver/transmitter circuit which is coupled to an ultrasonic transducer. Power is coupled to the echosonometer by electromagnetic induction through the animal's skin. Imaging signals from the echosonometer are electronmagnetically transmitted through the animal's skin to an external readout apparatus.

1 Claim, 9 Drawing Figures

ASTABLE MULTIVIBRATOR

DIFFERENTIATION

BUFFERED

CHARGE/DISCHARGE CYCLE OF H.V. PULSES TRANSMITTER

H.V. PULSE TRANSMITTER OUTPUT TO TRANSDUCER

OUTPUT OF AMPLIFIER & TRANSMITTED SIGNAL SHOWS TRANSMIT PULSE WITH AMPLIFIED ECHO SIGNALS

MINIATURE IMPLANTABLE ULTRASONIC ECHOSONOMETER

ORIGIN OF THE INVENTION

The invention described herein was made by an employee of the United States Government and may be manufactured and used by or for the Government for governmental purposes without the payment of any royalties thereon or therefor.

BACKGROUND OF THE INVENTION

1. Field of the Invention

The present invention relates generally to invasive biomedical ultrasonic imaging devices of the pulse-echo type.

2. Description of the Prior Art

Heretofore, real time remote examination of the internal structure of a biological organ, vessel, or tissue has been limited to the use of x-ray techniques, external ultrasonic imaging probes, implantable "transmission mode" ultrasonic imaging devices, and imaging apparatus of the transcutaneously hard-wired variety.

Imaging by x-ray has two significant limitations. X-rays are known to be harmful to both humans and animals. They should therefore be used with caution and for only short time intervals. Low energy ultrasound, on the other hand, has not been found to cause harm to biological organs, vessels or tissues. For this reason, it is preferred to use x-rays for long periods of real-time imaging. Another limitation of x-rays is its inability to image low density structures without employing special techniques. Ultrasound is able to image certain x-ray transparent objects. For example, unlike x-rays, ultrasound is able to image the thin mitral valve within the heart.

External ultrasonic imaging probes have been discussed in the paper "A Portable Battery Powered Ultrasonoscope," R. D. Lee et al. 25th ACEMB, October 1 - 5, 1972. These external imaging devices suffer from the disadvantage that in order to image the heart, they must transmit and receive ultrasonic impulses through the space between the ribs. As a result, certain portions of the heart cannot be seen since the ribs and sternum, as well as the lungs, obstruct the beam path of the external probe. Also there is some attenuation of the signal in the tissue between the transducer and the heart wall. In animal research it is very difficult to maintain beam alignment of an external probe over long periods. It is much more satisfactory to have the probe located at the actual site of interest.

An implantable ultrasonic transmission mode device has been discussed in the paper, "Miniature Implantable Sonomicrometer System," R. Lee and H. Sandler, *J. of Applied Physiology*, Vol. 28, No. 1, Jan. 1970. This device, due to its mode of operation, is only suitable for measuring the dynamic wallto-wall cardiac dimension; detailed intervening structures are not visible. The device is powered by batteries, batteries which are necessarily small so that they can be implanted in a patient. Accordingly, this device has a short operational period.

The last technique involves attaching an ultrasonic transducer to the organ wall and hard-wiring the lead out through the skin to external processing instrumentation. This method enables the imaging of all sections of the heart; however, there is a high risk of an infection occurring at the site where the wires exit from the skin.

BRIEF SUMMARY OF THE INVENTION

It is therefore one object of the present invention to provide an improved biomedical echosonometer.

It is another object to provide an improved biomedical echosonometer which is safe for long periods of real-time imaging.

It is yet another object to provide an improved biomedical echosonometer which has good resolution of fine structures.

It is a further object to provide an improved biomedical echosonometer which is able to image organs, vessels and tissues which are inaccessible to external probes.

It is a yet further object to provide an improved biomedical echosonometer which contains no batteries, and is fully implantable with no wires extending out through the skin.

The objects of the present invention are achieved by a miniature echosonometer intended for implantation within an animal's body. The miniature echosonometer includes a power receiver loop, a receiver/transmitter circuit, an ultrasonic transducer, and a signal transmitter loop. The echosonometer contains no power source. Power is electromagnetically induced into the power receiver loop from a power transmitter outside the body of the animal. High voltage pulses are generated in the receiver/transmitter circuit and coupled to the transducer where they are converted to ultrasonic energy Ultrasonic echoes reflected from interfaces within the organ or vessel under examination produce echo signals within the transducer and receiver/transmitter circuit. The echo signals are transmitted from the signal transmitter loop (within the animal's body) to an external readout by means of electromagnetic induction.

An important feature of the invention is the capability for imaging the heart without obstruction from the surrounding rib cage and the ability to maintain transducer alignment over long periods for trend analysis.

The foregoing as well as other objects, features, and advantages of the present invention will become more apparent from the following detailed description taken in conjunction with the appended drawings.

DESCRIPTION OF THE PREFERRED EMBODIMENT

Figure 1:
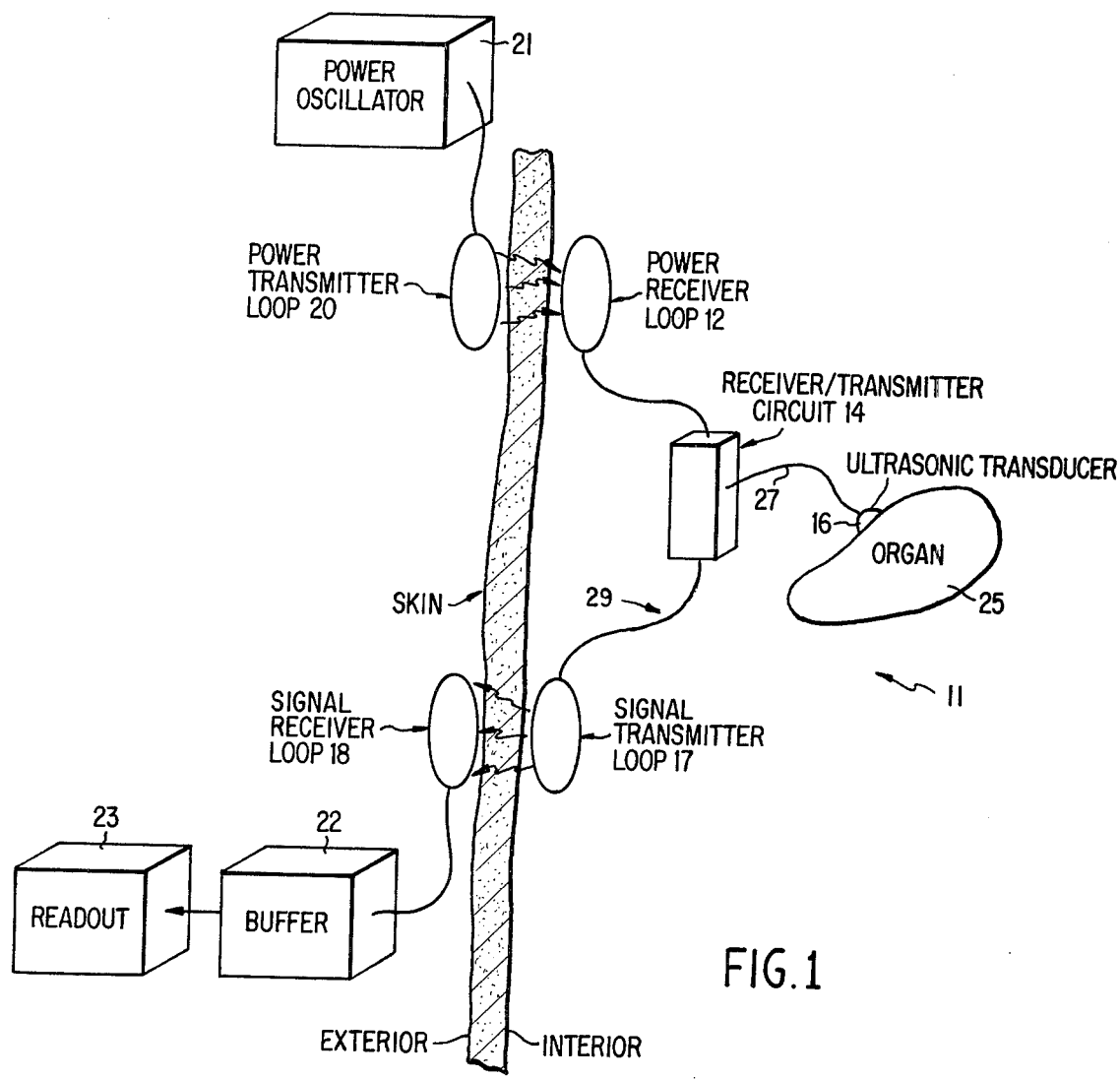
FIG. 1 is a block diagram of an ultrasonic biomedical measuring and recording apparatus incorporating the miniature, implantable echosonometer of this invention.

Referring to FIG. 1, the echosonometer 11 is surgically implanted within a suitable location in the animal under observation. The echosonometer comprises a receiver-transmitter circuit 14, an ultrasonic transducer 16, and a signal transmitter loop 17. The ultrasonic transducer 16 is attached, preferably by stitches, to the organ or artery 25 that is to be observed. Receiver-transmitter circuit 14 generates a stream of high-voltage pulses on connector 27 that causes transducer 16, a piezoelectric crystal, to periodically oscillate at an ultrasonic frequency. it has been found, for example, that a resonant frequency of 2.25 MHz produces favorable results when monitoring a heart organ. Reflection of ultrasonic energy from interfaces in organ 25 cause transducer 16 to oscillate and generate electrical "echo" signals. The time between a transmitted ultrasonic burst and a received echo is representative of the depth of ultrasonic energy penetration in the organ 25. When an organ such as the heart is bombarded with ultrasonic energy, numerous echoes are produced from the interfaces therein (chamber walls, mitral valve, etc.). The echo signals are amplified in receiver-transmitter circuit 14 and routed through connector 29 to signal transmitter loop 17 which comprises multiple turns of wire. The amplified echo signals are radiated from the loop 17 through the animal's skin to a signal receiver loop 18 which is located near the exterior surface. Loop 18 is also comprised of a number of turns of wire and the signal induced in the loop is fed to a readout 23 by means of a buffer circuit 22. Buffer circuit 22 may comprise, for example, means for matching the impedance of the loop 18 to readout 23 and amplification means. Readout 23 may be a recorder, such as an oscillographic recorder, or an oscilloscope. If readout 23 is an oscillographic recorder, buffer circuit 22 may include a pulse generator for furnishing synchronizing pulses to the recorder. The echo signals may be displayed on the oscilloscope in the "A" scan mode, for example, wherein the ordinate represents reflection signal amplitude and the abscissa represents distance from the transducer to a reflection interface in the object under observation. A more complex visual presentation, an "M" scan presentation, can be produced by utilizing an oscilloscope with a Z-axis input and a sweep generator with a ramp waveform for the Y axis. In the "M" scan mode the CRT trace is intensity modulated, the ordinate represents elapsed time, and the abscissa again represents the depth into the object examined from a baseline starting at the face of the transducer.

There are no batteries contained within receiver/transmitter circuit 14. Power for the circuit is obtained from power oscillator 21 which generates r-f energy to power transmitter loop 20. Power transmitter loop 20, a coil is situated in proximity to power receiver loop 12 (also a coil) and a-c power is electromagnetically induced in the latter. The induced power is rectified and filtered in receiver/transmitter circuit 14 to provide necessary d-c voltages for the active devices and circuits in receiver/transmitter circuit 14.

Figure 2:
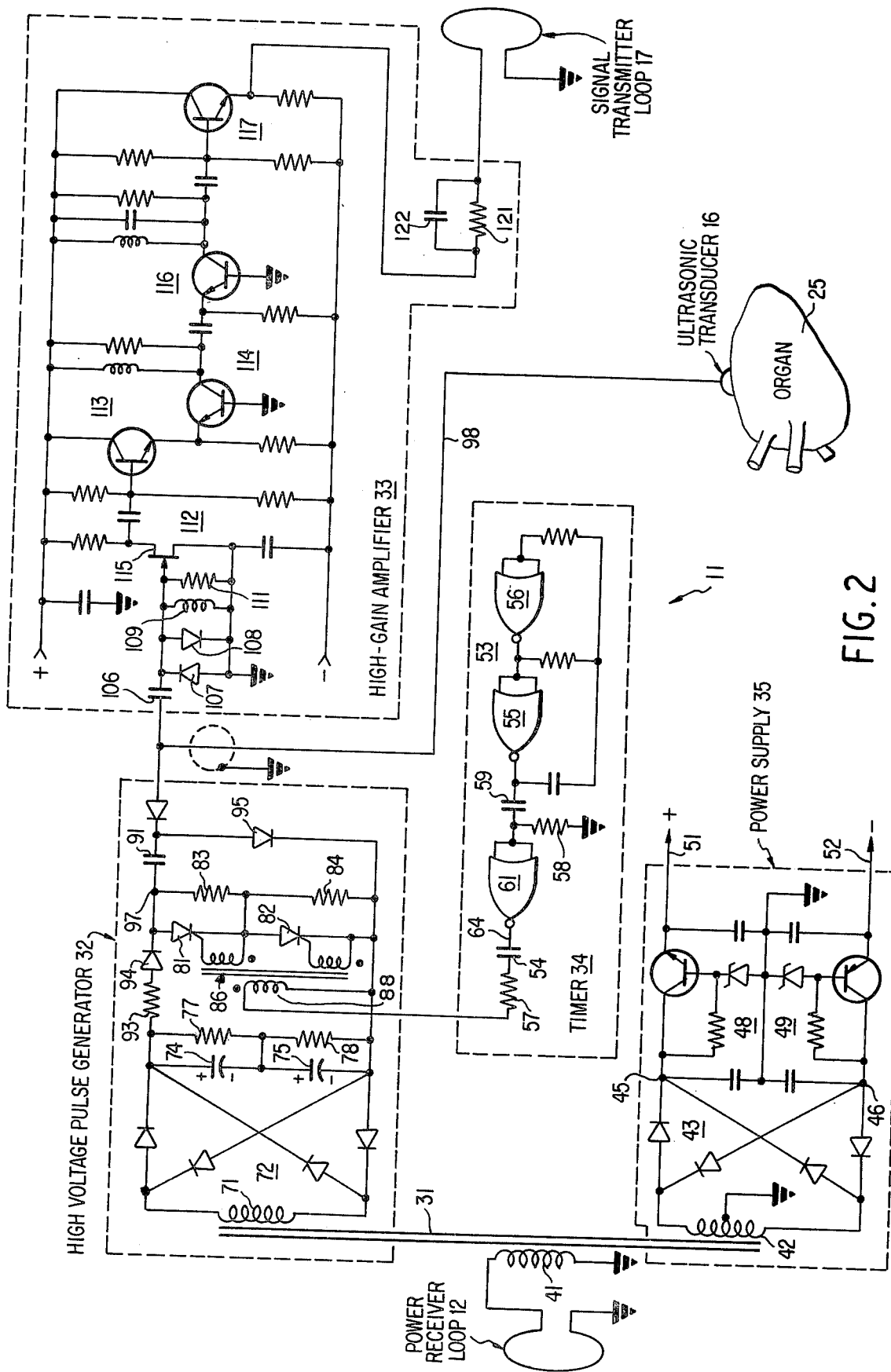
FIG. 2 is a detailed circuit diagram of the preferred embodiment of the echosonometer of this invention.

FIG. 2 is a detailed circuit diagram of the echosonometer 11. The echosonometer 11 includes power receiver loop 12, a high-voltage pulse generator 32, a high-gain amplifier 33, a timer 34, a power supply 35, signal transmitter loop 17 and ultrasonic transducer 16. High-voltage pulse generator 32 produces a train of pulses for periodically energizing ultrasonic transducer 16. The pulse rate of generator 32 is controlled by timer 34. Echo signals produced in transducer 16 are amplified in high-gain amplifier 33 and electromagnetically radiated from subcutaneous signal transmitter loop 17 to signal transmitter loop 18 positioned above the animal's skin.

Power supply 35 provides the operating power for timer 34 and high-gain amplifier 33.

The high frequency a-c energy electromagnetically induced in power receiver loop 12 by power transmitter loop 20 is coupled to the primary winding 41 of transformer 31. The low voltage output of secondary winding 42 is rectified by rectifier 43, filtered by capacitors 45, 46 and regulated by series regulators 48, 49. The positive voltage at output 51 is used to power the timer 34 and the high-gain amplifier 33, and the negative voltage at output 52 also energizes the amplifier.

Figure 3A:
FIG. 3(*a*) to (*f*) is a series of waveforms produced at various points in the detailed circuit diagram of FIG. 2.
Figure 3B:
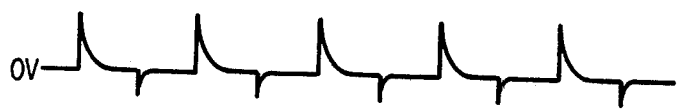
Figure 3C:
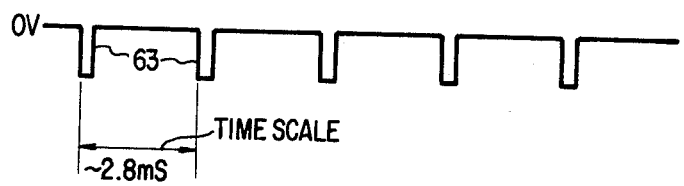

Timer 34 includes a conventional astable multivibrator 53 having dualinput NOR gates 55, 56 which are preferably CMOS integrated circuits. The square wave output of the astable multivibrator 53, see FIG. 38 a), is differentiated by an R-C circuit comprising resistor 58 and a capacitor 59. The differentiated waveform, see FIG. 3(b), is buffered by another dual-input NOR gate 61 to provide a series of negative clock pulses 63 on lead 64. These pulses are illustrated in FIG. 3(c).

Figure 3D:
Figure 3E:

Referring to the high-voltage pulse generator 32, a secondary winding 71 has many more turns than winding 42 and as a result a higher a-c voltage is induced therein. The induced a-c voltage is rectified by bridge rectifier 72 and filtered by capacitors 74 and 75. By using two capacitors in series, it is possible to select tantalum type capacitors. Tantalum capacitors have a high capacity-to-volume ratio and their usage helps keep the volume of the system small. Resistors 77 and 78 are in shunt with capacitors 74 and 75, respectively. Resistors 77 and 78 have equal resistance and they divide the filtered d-c voltage equally between the capacitors. The resistors insure that the capacitors will not unequally share the d-c voltage and cause one capacitor to exceed its voltage rating. Negative timing pulses 63 are coupled through capacitor 54 and resistor 57 to the primary 88 of pulse transformer 86. Every time that a negative pulse is impressed on the primary winding, positive pulses appear at the gates of silicon-controlled rectifiers 81 and 82 and cause them to fire. Resistors 83 and 84 have equal resistance and they distribute the voltage equally across the SCRs for protection and to prevent premature firing of the SCRs. Capacitor 91 is charged by the filter circuit through a charging path including current-limiting resistor 93, and diodes 94, 95. The SCRs 81, 82 constitute series-connected high speed switches that discharge capacitor 91 on each occurrence of a timing pulse 63. FIG. 3(d) depicts the waveform at junction 97. When the SCRs are triggered, the positive electrode of capacitor 91 is connected to ground, capacitor 91 is rapdily discharged, and a high-voltage, short-duration, negative pulse 101 (see FIG. 3(e)) is sent to ultrasonic transducer 16 via lead 98. Pulse 101 causes the transducer 16 to vibrate and emit a burst of ultrasonic energy through organ 25. Reflections of energy from the organ interfaces produce vibrations in the transducer and echo signals on lead 98.

Figure 3F:
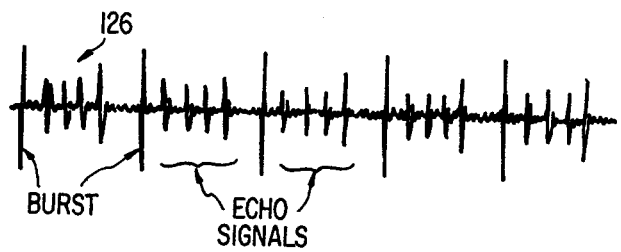

The echo signals are channeled through coupling capacitor 106 and amplified in high-gain amplifier 33 which includes three voltage amplifiers 112, 114, 116 and two emitter followers 113, 117. Capacitor 106 and clipping diodes 107, 108 protect the first amplifier stage 112 from being damaged by the highvoltage pulses 101. The low level echo signals are not clipped by diodes 107 and 108. Inductance 109 serves as a low resistance path for d-c voltage and biases the gate of FET 115 at ground potential. Resistor 111 lowers the Q of the amplifier input circuit and broadens the bandwidth of the amplifier. The amplifier converts the weak electrical echo signals to an appropriate level for the signal transmitter loop 17 which is coupled to emitter follower 117 by means of shunt-connected resistor 121 and capacitor 122. The signal transmitter loop 17 is a small, subcutaneously located, multi-turn induction coil. The amplified echo signals (along with clipped pulses derived from pulses 101) 126, shown in FIG. 3(f), are electromagnetically radiated from signal transmitter loop 17 and received by signal receiver loop 18 which is stationed above the animal's skin near loop 17.

Once the echosonometer is surgically implanted in the animal's body, it may be operated as long as desired — for weeks, for months or longer. The usage period is not dictated by the life of a battery as the echosonometer contains no batteries. Further, the patient is not encombered with wires passing through the skin.

Figure 4:
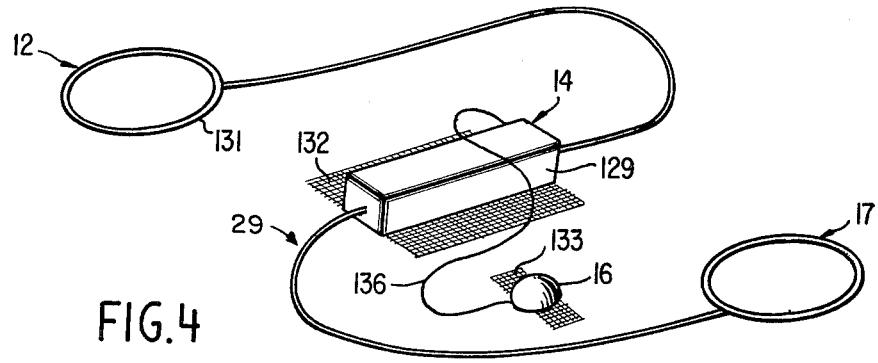
FIG. 4 is an isometric view of the exterior structure of the echosonometer of this invention.

Referring to FIG. 4, there is illustrated in isometric view, the exterior structure of the echosonometer 11. Container 129 has three shielded compartments. One compartment holds transformer 31. The second compartment houses the dual-voltage power supply 35, the timer 34, and high-voltage pulse generator 32. The third chamber isolates the high-gain amplifier 33 from the other circuits. Container 129 is completely coated with silicon rubber and a mesh 132 is partially embedded in the silicon rubber. Transducer 16 is coupled to the receiver/transmitter circuit 14 in container 129 by means of a coaxial cable 136 which preferably has a flexible stainless steel outer conductor and a silicon rubber outer jacket. All but the radiating face of transducer 16 is coated with silicon rubber and a mesh 133 is secured in the silicon rubber. Meshes 132 and 133 may be employed to anchor container 129 and transducer 16 within the body of the subject being examined. Mesh 133, could, for example, encircle an artery or be stitched to an organ. In some situations, clamps may be more convenient than sutures.

In an actual model of the preferred embodiment, the following values, dimensions, or components were employed:

Power Oscillator Frequency: 230 KHz
Timer Frequency: 350 Hz
Ultrasonic Frequency: 2.25 MHz
SCRs 81, 82 Unitrode GA 201A
Loop 12 8T, #30 AWG, 7.3 cm diameter
Loop 17 15T, #30 AWG, 7.3 cm diameter Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. An implantable biomedical echosonometer for taking real-time dimensional measurements of an organ in an animal comprising:
  A. a sealed implantable assembly comprising:
    a. a power receiver loop,
    b. a transformer with a primary winding and low and high voltage secondary windings; said power receiver loop being coupled to said primary winding, said loop being remote from said primary winding whereby said loop can be easily located directly below said animal's skin;
    c. means for converting the output of said low voltage winding to a regulated d-c voltage;
    d. means for producing timing pulses;
    e. means coupled to said high voltage winding and said producing means for generating high voltage pulses at a rate set by said timing pulses;
    f. an ultrasonic transducer adapted to be affixed to the organ to be measured;
    g. a signal transmitter loop; and
    h. a high gain amplifier powered by said regulated d-c voltage, the input of said amplifier being coupled to said pulse generating means and said transducer, the output of said amplifier being coupled to said signal transmitter loop, said amplifier being operable to amplify the pulses from said pulse generating means and echo waveforms received by said transducer caused by ultrasonic reflections from interfaces in said organ, said signal transmitter loop being remote from said amplifier so that said signal transmitter loop can be easily positioned directly beneath said animal's skin;
  B. a power transmitter loop adapted to be disposed outside the animal's skin near said power receiver loop;
  C. a power oscillator connected to said power transmitter loop, said oscillator and loop being operable to inductively transmit electric power to said power receiver loop;
  D. a signal receiver loop adapted to be disposed outside said animal's skin near said signal transmitter loop; and
  E. means for reading out signals inductively coupled to said signal receiver loop from said signal transmitter loop.

* * * * *